(12) United States Patent
Vladiskovic et al.

(10) Patent No.: US 8,314,241 B2
(45) Date of Patent: Nov. 20, 2012

(54) PROCESS FOR THE PREPARATION OF CRYSTALLINE DEXLANSOPRAZOLE

(75) Inventors: Chiara Vladiskovic, Milan (IT); Alessandro Restelli, Bareggio (IT); Gabriele Razzetti, Sesto San Giovanni (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 239 days.

(21) Appl. No.: 12/830,713

(22) Filed: Jul. 6, 2010

(65) Prior Publication Data

US 2011/0028728 A1    Feb. 3, 2011

(30) Foreign Application Priority Data

Jul. 29, 2009  (IT) ............... MI2009A1356

(51) Int. Cl.
C07D 401/12    (2006.01)
(52) U.S. Cl. .................................... 546/273.7
(58) Field of Classification Search ............... 546/273.7
See application file for complete search history.

(56) References Cited

U.S. PATENT DOCUMENTS

| 6,462,058 | B1 | 10/2002 | Fujishima |
|---|---|---|---|
| 6,664,276 | B2 | 12/2003 | Fujishima |
| 6,939,971 | B2 | 9/2005 | Fujishima |
| 7,285,668 | B2 | 10/2007 | Hashimoto |
| 2009/0163553 | A1 | 6/2009 | Fujishima |
| 2010/0204479 | A1* | 8/2010 | Vladiskovic et al. ...... 546/273.7 |
| 2011/0009637 | A1* | 1/2011 | Braga et al. ............... 546/274.4 |

FOREIGN PATENT DOCUMENTS

| AU | 88406/91 | | 11/1990 |
|---|---|---|---|
| EP | 1277752 | A1 | 1/2003 |
| EP | 1293507 | A1 | 3/2003 |
| EP | 1552833 | A1 | 7/2005 |
| ES | 2023609 | | 1/1992 |
| ES | 2060541 | | 11/1995 |
| WO | 9208716 | A1 | 5/1992 |
| WO | 9602535 | A1 | 2/1996 |
| WO | 2005054228 | A1 | 6/2005 |
| WO | 2009088857 | A1 | 7/2009 |
| WO | 2009117489 | A1 | 9/2009 |
| WO | 2011/004387 | A2 | 1/2011 |

OTHER PUBLICATIONS

Kirk-Othmer Encyclopedia of Chemical Technology, vo. 8, p. 95-147 (2002).*

* cited by examiner

*Primary Examiner* — Patricia Morris
(74) *Attorney, Agent, or Firm* — Rothwell, Figg, Ernst & Manbeck, P.C.

(57) ABSTRACT

Process for the preparation of crystalline anhydrous (R)-2-[[[3-methyl-4-(2,2,2-trifluoroetoxy)-2-piridyl]methyl]sulphinyl]benzimidazole (dexlansoprazole).

10 Claims, 1 Drawing Sheet

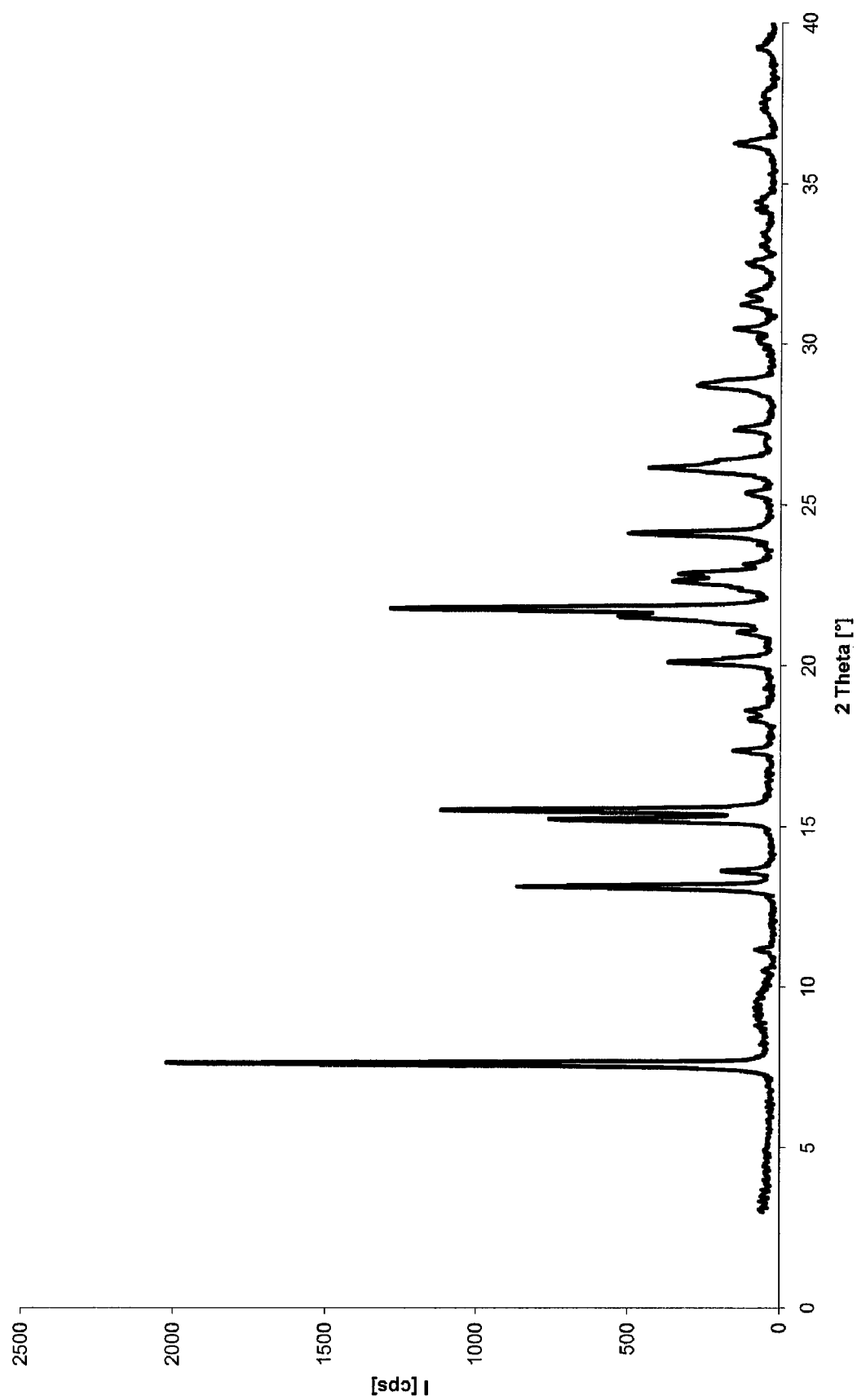

PROCESS FOR THE PREPARATION OF CRYSTALLINE DEXLANSOPRAZOLE

TECHNICAL FIELD

The present invention relates to a process for the preparation of crystalline anhydrous (R)-2-[[[3-methyl-4-(2,2,2-trifluoroetoxy)-2-piridyl]methyl]sulphinyl]benzimidazole (dexlansoprazole).

BACKGROUND ART

Dexlansoprazole, namely (R)-2-[[[3-mehyl-4-(2,2,2-trifluoroetoxy)-2-piridyl]methyl]sulphinyl]benzimidazole is an enantiomer of lansoprazole. Dexlansoprazole is a protonic pump inhibitor and is used in the treatment of diseases such as erosive aesophagitis, gastroesophageal reflux and gastrointestinal disorders. Dexlansoprazole is known from WO 92/08716, and disclosed in crystalline solid form in U.S. Pat. No. 6,462,058, in particular in crystalline anhydrous form (with a melting point of 147-148° C.) and sesquihydrate form (with a melting point of 76-80° C.), whereas amorphous dexlansoprazole is known from US 2009/0163553.

As disclosed in US 2004/0049045, crystalline anhydrous dexlansoprazole has a higher thermal stability than other solid forms of dexlansoprazole. The known processes for the preparation of crystalline anhydrous dexlansoprazole have a low industrial application, because of both the relevant degradation of the starting materials, due to the used reaction conditions, and the resulting low yields of crystalline anhydrous dexlansoprazole.

Thus, there is the need of an alternative, improved process for the preparation of crystalline anhydrous dexlansoprazole, easily applicable on industrial scale and with high yields.

SUMMARY OF THE INVENTION

It has been found that crystalline anhydrous dexlansoprazole, disclosed in U.S. Pat. No. 6,462,058, can be advantageously obtained by crystallization starting from an alcoholic solution of another crystalline or amorphous form of dexlansoprazole.

BRIEF DESCRIPTION OF THE FIGURES AND ANALYSIS METHODS

The obtained crystalline dexlansoprazole has been characterised by X-ray powder diffraction (XRPD), $^1$H-NMR nuclear magnetic resonance spectrometry, and differential scanning calorimetry (DSC). The water content of the compounds was determined by titration with the Karl Fischer technique. The X-ray diffraction spectra (XRPD) were collected with the APD-2000 automatic powder and liquid diffractometer manufactured by Ital-Structures under the following operating conditions: Bragg-Brentano geometry, CuKα radiation (λ=1,5418 Å), scanning with a 2θ angle range of 3-40° and a step size of 0.03° for a time of 1 sec. The $^1$H-NMR spectra were acquired with a Varian Mercury 300 spectrometer, using DMSO-d6 as solvent. The DSC thermograms were acquired with a Mettler-Toledo DSC 822e differential scanning calorimeter, under the following operating conditions: open aluminium capsule, range 30-300° C. at the rate of 10° C./min, with nitrogen as purge gas (80 ml/min).

FIG. 1. XRPD spectrum of crystalline anhydrous dexlansoprazole herein defined for better convenience Form ω, wherein the most intense peaks fall at 7.5, 11.4, 13.1, 13.5, 15.1, 15.4, 17.3, 20.0, 21.7, 22.5, 24.0, 26.1, 27.3 e 28.6±0.2° in 2θ.

The particle size and the $D_{50}$ value were determined with the known laser light scattering technique using a Malvern Mastersizer MS1 instrument in the following operating conditions:
300RF mm lens with 2.4 mm laser beam length;
500 mg sample dispersed in 10 ml of hexane (ACS reagent) with 1% of SPAN 85®, without pre-sonication, and with a stirring rate of 2500 rpm.

DETAILED DESCRIPTION OF THE INVENTION

The present invention relates to a process for the preparation of crystalline anhydrous dexlansoprazole comprising dispersing dexlansoprazole in an alcoholic solvent and dissolving it, cooling the solution to form a precipitate of crystalline anhydrous dexlansoprazole, and recovering the solid.

Dexlansoprazole used as starting material can be any known form thereof for example amorphous or crystalline hydrate dexlansoprazole, preferably amorphous or sesquihydrate dexlansoprazole.

An alcoholic solvent can be a straight or branched $C_1$-$C_6$ alkanol, preferably a $C_1$-$C_4$ alkanol, for example methanol, ethanol, isopropanol, 1-butanol, 2-butanol, or a mixture of two or more, preferably two or three of said solvents preferably ethanol, isopropanol or 2-butanol.

The concentration of dexlansoprazole in the alcoholic solution is typically comprised between about 5% and about 50%, preferably between about 10% and about 40%.

If desired, the dissolution of dexlansoprazole in the alcoholic solvent can be carried out by heating the dispersion of dexlansoprazole at a temperature which is not higher than 40° C., preferably at about 35° C.; and/or by adding from about 0.1 to about 1% v/v of water to the dispersion. If desired, in order to promote the subsequent crystallization, the alcoholic solution of dexlansoprazole can be submitted to azeotropic evaporation of the solvent under reduced pressure, in order to concentrate the solution, and then cooled to room temperature, preferably slowly, for example at a cooling rate comprised between about 0.1 and 0.4° C. per minute.

If desired, to fluidify the dispersion and thus to facilitate the subsequent crystallization, a solvent in which dexlansoprazole is not soluble can be added to the alcoholic solution, typically a $C_5$-$C_9$ alkane, preferably hexane or heptane.

The cooling of the solution, to form a precipitate of crystalline anhydrous dexlansoprazole, can be carried out at a temperature comprised between about 0° C. and about 10° C., preferably slowly, for example at a cooling rate comprised between about 0.1 and 0.4° C. per minute.

If desired, the crystallization can be carried out by seeding with the desired crystalline form.

The recovery of crystalline anhydrous dexlansoprazole can be carried out by known techniques, for example by filtration or by centrifugation, preferably by filtration on Bückner filter.

The so obtained crystalline anhydrous dexlansoprazole has a water content comprised between about 0 and about 1% w/w, preferably between about 0.05 and 0.5%, more preferably between 0.1 and 0.3%, so as to be defined substantially anhydrous. The product has the same characteristics of the crystalline anhydrous form disclosed in U.S. Pat. No. 6,462,058, having a m.p. 147-148° C.

The size of the so obtained fragments of crystalline anhydrous dexlansoprazole is characterized by a $D_{50}$ value comprised between about 25 and about 250 μm. If desired, such value can be reduced by micronisation or fine grinding.

Crystalline anhydrous dexlansoprazole obtained according to the process of the invention has a purity equal to or higher than 99%, preferably equal to or higher than 99.5%.

The following examples illustrate the invention.

Example 1

Preparation of Crystalline Anhydrous Dexlansoprazole Starting from Amorphous Dexlansoprazole 20.0 g of amorphous dexlansoprazole are dispersed in 80 ml of isopropanol and the dispersion is heated at about 35° C. The solid at the beginning dissolves and then starts to precipitate again. The dispersion is slowly cooled (0.2° C./min) till to about 20° C., and then 100 ml of hexane are dropped therein in about 45 min. The dispersion is again slowly cooled till to 0° C. and the solid is recovered by filtration. The solid is washed on the filter with isopropanol and hexane.

The obtained product has a XRPD spectrum, as reported in FIG. 1.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; s (3H). 2.16 ppm.

Example 2

Preparation of Crystalline Anhydrous Dexlansoprazole Starting from Dexlansoprazole Sesquihydrate 50.1 g of dexlansoprazole sesquihydrate are dispersed in 200 ml of 2-butanole and the dispersion is heated at 35° C. till the dissolution is complete. The solution is cooled to 20° C. at a cooling rate of 0.3° C./min, and then seeded with crystalline anhydrous dexlansoprazole. 400 ml of heptane are slowly dropped therein, and the solution slowly cooled to 0° C. and the solid recovered by filtration.

m.p. 148-150° C.

The obtained product has a XRPD spectrum, as reported in FIG. 1 and a $H^1$-NMR spectrum as reported in Example 1.

Example 3

Preparation of Crystalline Anhydrous Dexlansoprazole Starting from Amorphous Dexlansoprazole 139 g of amorphous dexlansoprazole are dissolved in 1390 ml of isopropanol and 10 ml of water at a temperature of 25° C. About 1000 ml of solvent are distilled off and the solution is cooled to room temperature. Then 1000 ml of heptane are slowly dropped therein. The solution is slowly cooled to 0° C. and the solid is recovered by filtration.

m.p. 148-150° C.

The obtained product has a XRPD spectrum, as reported in FIG. 1 and a $H^1$-NMR spectrum as reported in Example 1.

Esempio 4

Preparation of Crystalline Anhydrous Dexlansoprazole Starting from Dexlansoprazole (KF 3,5%)

10 g of dexlansoprazole are dissolved in 20 ml of ethanol at the temperature of 25° C. 60 ml of heptane are slowly dropped therein and then the solution is slowly cooled to 0° C. and the solid is recovered by filtration.

The product has a XRPD spectrum, as reported in FIG. 1 and a $H^1$-NMR spectrum as reported in Example 1.

The invention claimed is:

1. A process for the preparation of crystalline anhydrous dexlansoprazole having an XRPD wherein the most intense peaks fall at 7.5, 11.4, 13.1, 13.5, 15.1, 15.4, 17.3, 20.0, 21.7, 22.5, 24.0, 26.1, 27.3 and 28.6±0.2° in 2θ, comprising dispersing dexlansoprazole in an alcoholic solvent and dissolving it by heating the dispersion of dexlansoprazole at a temperature not higher than 40° C.; cooling the solution at a temperature between 0° C. and 10° C. to form a precipitate of crystalline anhydrous dexlansoprazole; and recovering any solids.

2. The process according to claim 1, wherein the alcoholic solvent is a straight or branched $C_1$-$C_6$ alkanol.

3. The process according to claim 1, wherein the dissolution of dexlansoprazole in the alcoholic solvent is carried out by adding from 0.1 to 1% v/v of water to the dispersion.

4. The process according to claim 1, wherein the cooling is carried out slowly.

5. The process according to claim 1, wherein the cooling is carried out at a cooling rate comprised between 0.1 and 0.4° C. per minute.

6. The process according to claim 1, wherein before the cooling the alcoholic solution is submitted to azeotropic evaporation.

7. The process according to claim 1, wherein before the cooling of the solution, a solvent in which dexlansoprazole is not soluble is added.

8. The process according to claim 7, wherein the solvent is a $C_5$-$C_9$ alkane.

9. The process according to claim 1, wherein the crystalline anhydrous dexlansoprazole has a purity equal to or higher than 99%.

10. The process according to claim 9, wherein the crystalline anhydrous dexlansoprazole has a purity equal to or higher than 99.5%.

\* \* \* \* \*